United States Patent [19]
Sollish

[11] 4,028,934
[45] June 14, 1977

[54] ULTRASONIC STEREOSCOPIC IMAGING DEVICE

[75] Inventor: Bruce D. Sollish, Rehovot, Israel

[73] Assignee: Yeda Research & Development Co. Ltd., Rehovot, Israel

[22] Filed: Nov. 4, 1975

[21] Appl. No.: 628,751

[52] U.S. Cl. .................. 73/67.8 S; 73/67.5 H
[51] Int. Cl.² .............................. G01N 29/04
[58] Field of Search ...... 73/67.5 R, 67.5 H, 67.8 R, 73/67.8 S, 67.9; 340/3 R, 3 T

[56] References Cited
UNITED STATES PATENTS

| 3,781,775 | 12/1973 | Malloy et al. | 340/3 R |
| 3,881,164 | 4/1975 | Kossoff | 73/67.8 S |
| 3,936,791 | 2/1976 | Kossoff | 73/67.8 S |

FOREIGN PATENTS OR APPLICATIONS 941,771  11/1963  United Kingdom ............ 73/67.8 S Primary Examiner—James J. Gill
Attorney, Agent, or Firm—Browdy and Neimark

[57] ABSTRACT

An apparatus for three-dimensional visualization of an object or substance with particular utility for determining the presence of breast cancer contains a dual sensing head having two transducers connected to conventional B-scan equipment. The methodology of this apparatus is based on a new form of ultrasonic imaging that presents perspective views rather than tomograms (cross-sections). These two perspective views are obtained simultaneously by using a pair of cylindrically focused transducers in a scanning unit and are displayed on a monitoring scope in a split screen presentation, which, when viewed as a stereo pair, gives the operator a three-dimensional image of the interior of the scanned object.

7 Claims, 7 Drawing Figures

ULTRASONIC STEREOSCOPIC IMAGING DEVICE

FIELD OF THE INVENTION

The present invention relates to an apparatus for three-dimensionally viewing the interior of an object, and has particular utility in the field of breast cancer diagnoses.

BACKGROUND OF THE INVENTION

Breast cancer screening clinics have been established to help in early detection of breast cancer, a major cause of death in women where asymptomatic women are encouraged to come to the clinic for annual examinations. When a suspected lesion is found, the woman is directed to see her physician for treatment.

No single method of examination has been found to give 100% detection probability. Instead, a combination of tests is performed, each of which probes a different aspect of possible breast cancer. The first is a check of family history for possible genetic susceptibility to breast cancer. The second is a physical examination (palpation) for detecting growths large enough to be felt. The third is mammography (soft x-ray imaging) for identifying tumors, whose increased density over normal tissue results in increased x-ray absorption. The fourth is thermography, which uses an infrared camera and display system to detect hot spots, indicative of abnormally high blood flow, an area characteristic of a tumor.

Even the above combination of tests, while more effective than any single test, is not successful in detecting every tumor. However, it has been discovered that ultrasonic imaging is ideally suited for examination of soft tissue structure such as the breast. Ultrasound is sensitive to composition, density, elasticity, shape and orientation. Since a tumor differs in these respects with the host medium, it should be detected with ultrasonic imaging. Because ultrasonic wavelengths of less than 1 mm can effectively penetrate the breast, tumors as small as several mm in diameter can be detected.

Pulse-echo ultrasonic imaging techniques have been applied in medical diagnoses for over 20 years. This type of imaging is especially attractive for medical applications for the following reasons:

a. The low acoustic intensities used in diagnostic ultrasound are typically less than 10 mW/cm$^2$, which are several orders of magnitude below the threshold intensities for damage to sensitive tissues and organs.

b. This type of imaging has particular facility in the display of soft tissue structures. Because the absorption of ultrasound by muscle and fat is typically in the range of 0.5 – 2.0 db/MH/cm, at 2.25 MH, ultrasound passing through fatty tissue is attenuated by approximately 10 db at 10 cm.

A tumor embedded in normal tissue will reflect a different pulse and in general, this echo pulse will differ in all respects from its surroundings.

The simplest form of imagining is the A-scan, or time-amplitude ultrasonography. This type of scan system contains an ultransonic transducer and a scanning device which includes a pulse generator, a receiver-processor, and a monitor oscilloscope. To record an A-scan, the transducer is first placed on the area of interest or coupled to it by a suitable coupling medium such as water. A high voltage pulse is applied to the transducer, which emits a burst of ultrasound that enters the target. The transducer is well damped for good axial resolution, and in general contains a spherical lens to focus the ultrasonic output to a thin beam. A portion of the incident ultrasonic beam is backscattered whenever the beam encounters an interface between two media having different acoustic impedances (due to different densities or elasticities) or passes through an inhomogeneous (heterogeneous) medium.

The backscattered sound, i.e. echoes, is reflected back to the transducer and is processed by the receiver and displayed on the monitor as a train of pulses. The amplitude of a pulse is proportional to the amplitude of the reflected ultrasound, while the position and time of the pulse is proportional to the distance of the corresponding echo producing interface from the transducer (provided that the propagation velocity is constant). Therefore, this type of scan has the capacity to indicate that the tumor is present in normal tissue, however, its exact position, shape and form cannot be determined.

A more comprehensive form of ultrasonic imaging is a B-scan, or ultrasonic tomogram. This method involves scanning a transducer across the target, by translation of the transducer alone or by both translating and rotating the transducer. As was true in the A-scan, echoes picked up by the B-scan transducer are processed by the receiver. However, the amplified echoes are fed to a monitor unit which generates a series of dots corresponding to the echoes received. The horizontal and vertical imputs of the monitor unit are controlled by position and angle sensing potentiometers linked to the movement of the transducer. Therefore, at any given moment, the position and orientation of the transducer are duplicated on the display. The dots then represent interfaces encountered by the ultrasonic beam at that particular orientation and a continuous scan generates a complete cross section which can be photographed in a time exposure or viewed on a storage screen.

However, since the B-scan method of ultrasonography only produces cross-sectional images, the location of a possible breast tumor at an arbitrary site would require a time consuming series of parallel and closely spaced scanning operations, typically on the order of 100 scans. Clearly then another method of ultransonic imaging is needed which would reduce the required number of views.

A B-scan method has been developed which reduces the number of scans to approximately 20. This method is called ultrasonic stereography and involves halographic processing of the B-scans before viewing the final image. The reconstructed image to be truly three-dimensional can be viewed naturally with illumination from a Tensor-type light source, without the need for a laser or a stereo viewer. The physician can look at the breast from different viewpoints (using the virtual image reconstructed by the stereohologram) or can selectively examine any plane through the breast (by placing a ground glass screen in the real image reconstructed by the stereohologram). However, this method still requires a significant number of scans, does not give instantaneous results, and requires a step of holographic processing.

SUMMARY OF THE INVENTION

It is accordingly an object of the present invention to overcome the defects of the prior art as described above.

A further object is to provide three-dimensional viewing of tumors.

Another object of the present invention is to provide an apparatus for three-dimensionally viewing a certain object.

Yet another object of the present invention is to provide an apparatus for three-dimensionally locating a region having different properties than the surrounding material.

Still a further object of the present invention is to provide a device for determining the presence of a tumor in a living organ or tissue.

Another object of the present invention is to provide a device for determining the presence of a tumor in a human breast.

Still another object of the present invention is to produce a device for determining the presence of a tumor in the human breast which is easy to operate and allows for the patient's saftey and comfort.

A still further object of the present invention is to produce a device which can detect lesions of a few millimeters in diameter and which provides immediate results.

These and other objects of the present invention are fulfilled by a safe and simple apparatus for the generation and display of an ultrasonic stereoscopic imaging device containing a scanning head, and an electronic signal generating, processing and display unit. The scanning head can translate and rotate and contains at least two transducers having slightly different axes of propagation. These transducers are electrically connected to a generating means which generates a series of high voltage electrical pulses which are changed to sonic energy by the transducers and are then transmitted to a target area which reflects sonic energy back to the transducers. These transducers then convert the sonic energy into electrical pulses which are displayed side-by-side on a display screen. A transducer multiplexer and a display multiplexer are provided in this device to effectively isolate the pulses which are transmitted and received by each of the transducers. A stereo viewer is attached to the display screen and the physician or technician who is operating the entire unit can view the two images as one three-dimensional image and therefore, by different consistencies of the image, can determine whether there appears any area having a different composition than the surrounding area. If this device is used to determine the presence of a breast cancer, this area of different composition would denote the possible presence of such a lesion.

This device reduces the number of scans required to a single dual scan. The results are available for viewing immediately without the need for holographic processing.

Additionally, the ultrasonic imaging device could provide information for different medical diagnoses, such as to distinguish between a cystic and fibrous mass since the former shows up as an outline, and the latter is full of echoes.

BRIEF DESCRIPTION OF THE DRAWING

The above and additional objects inherent to the present invention will become more apparent by reference to the description of an illustrated embodiment and a drawing thereof in which.

DETAILED DESCRIPTION OF PREFERRED EMBODIMENTS

The basic element of this apparatus is a dual transducer scanner 10, using a cylindrically focused transducer 22 wherein the X axis denotes the propagation direction, the Y axis the scan direction, and the Z axis the projection direction. Although the exact configuration and properties of the transducer are not crucial, it is found that satisfactory results for medical diagnoses are achieved using a transducer having a frequency of 2.25 MHz and a focal length of 4 inches with a length of 3 inches, width of ½ inch and a thickness of 2 inches. The transducers used, however, should be selected for low ringing to optimize resolution in the direction of propagation and for narrow beam width in the focal region to optimize transverse resolution. The transducers can be mounted in individual or joint water baths and are placed in a scanner head and connected to a mechanical movement arm (not shown). Cylindrically focused transducers are used in this invention since they exhibit narrow beam width in one transverse dimension.

Figure 7:
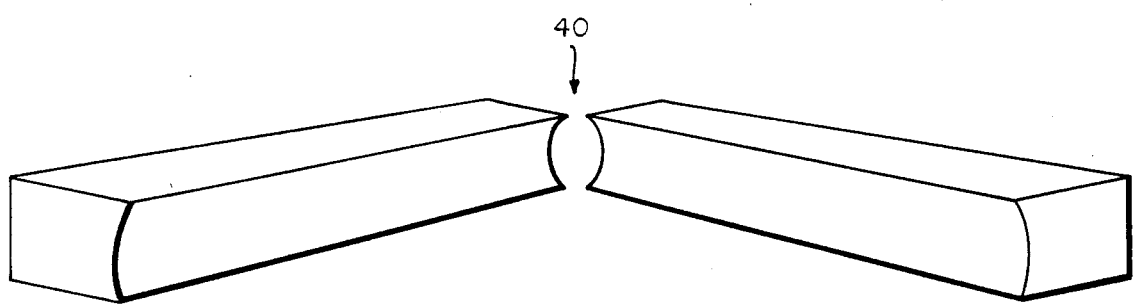
FIG. 7 is a perspective view of another pair of cylindrically focused transducers.
Figure 6:
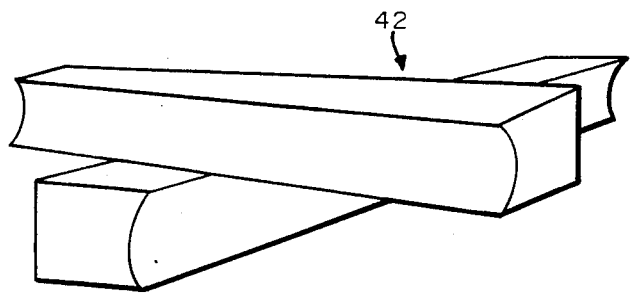
FIG. 6 is a perspective view of a pair of cylindrically focused transducers.

The transducers are arranged in either a V or X (see FIGS. 6 and 7) configuration, depending upon the distance to the target. It has been found that the X configuration is most suited for relatively close targets, while the V configuration is better for relatively distant targets. Since the principles of operation are similar, for clarity, only the V configuration will be discussed. Both the X and V configurations shown in FIGS. 6 and 7 respectively show normals, intersecting the transducer elements at approximately 30°. However, this was only done for clarity, since the actuality the angle is approximately 5°.

Figure 1:
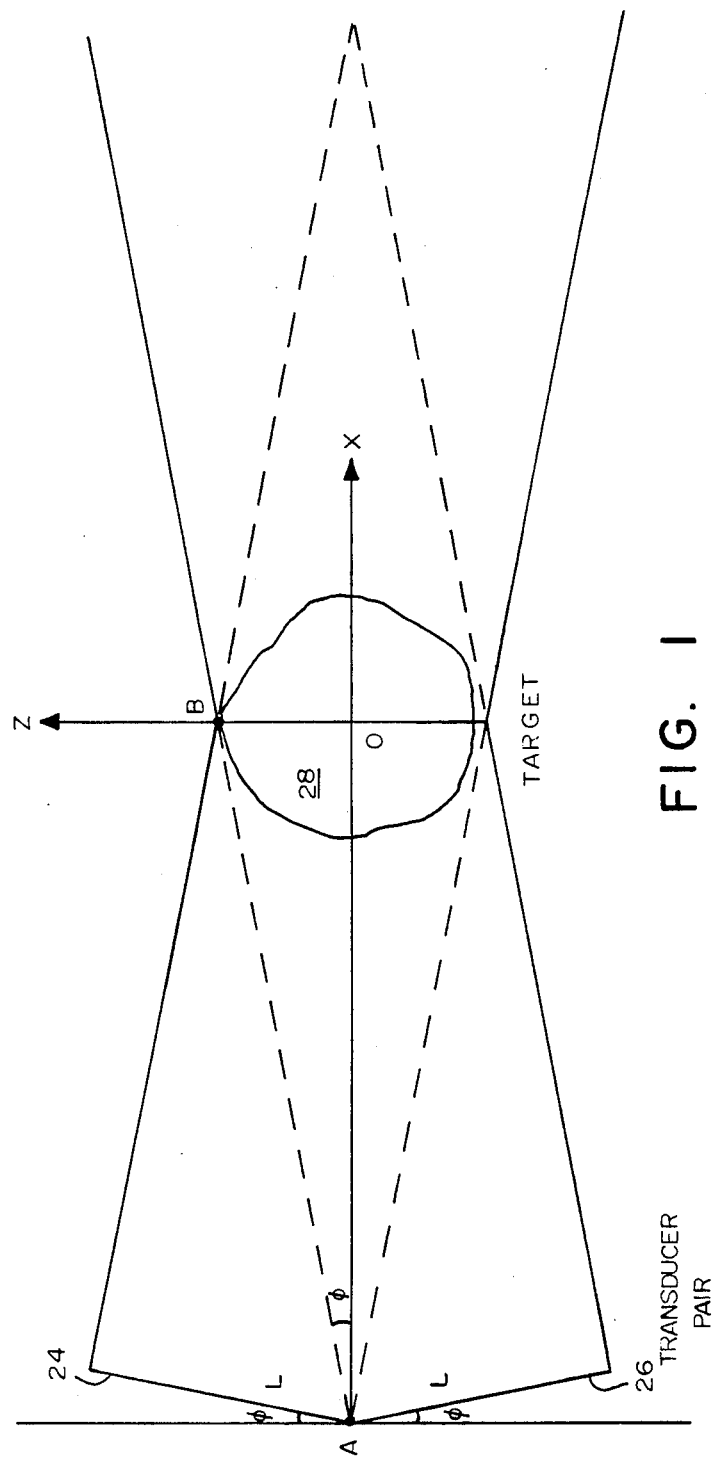
FIGS. 1–3 exhibit the scanning geometry which is used in this invention.
Figure 5:
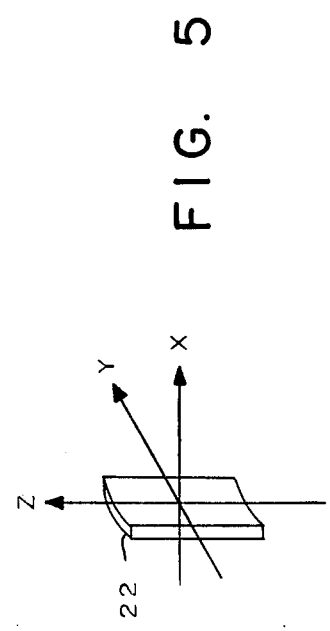
FIG. 5 is a perspective view of a cylindrically focused transducer.
Figure 2:
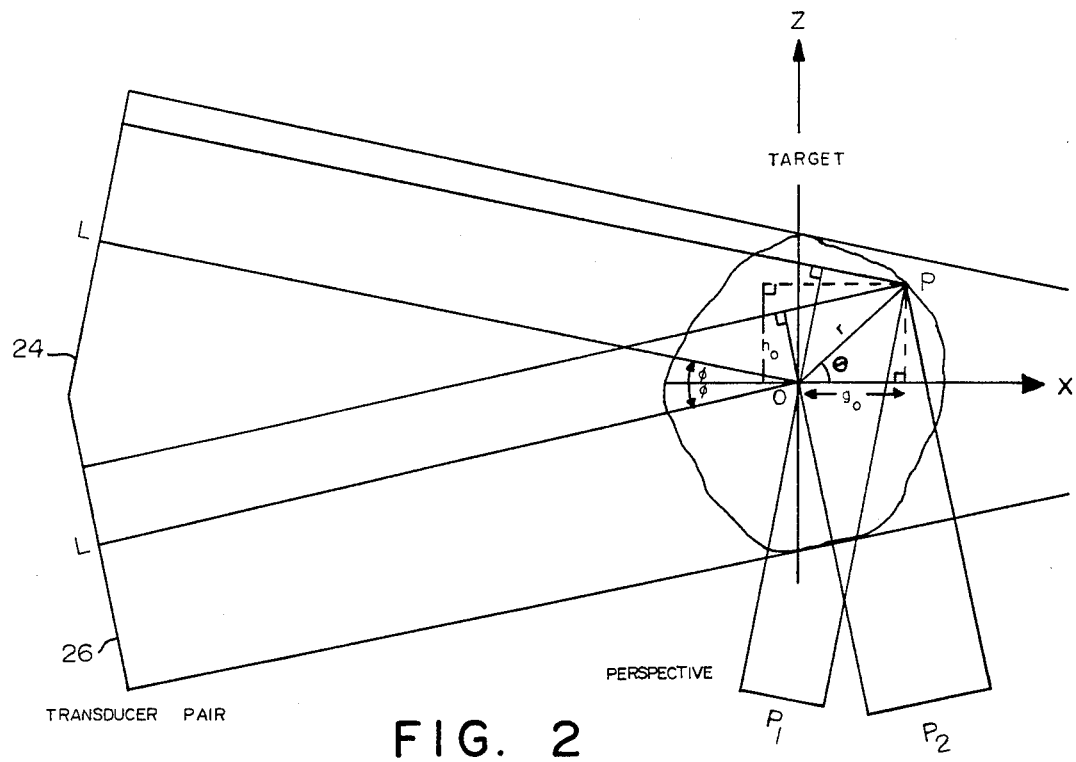

FIG. 1 shows the scanning geometry which is utilized and shows transducer elements 24 and 26 having a length L arranged in an elongated V configuration. If the X configuration was utilized (FIG. 6), one of the transducers would be mounted slightly above the other with its axis of propagation slightly offset. Normals to the transducer elements intersect at an angle of 2 $\phi$, as shown in FIG. 2, where typically 2 $\phi = 5°$. These transducers are assumed to act as ideal line sources in the plane of the figure and therefore the beams would overlap as shown by the area within the dashed lines. Consequently, for this invention to properly operate, the target area 28 must lie in this region. As shown in FIG. 1, the best location for the center of this target is $X = L/2 \sin \phi, Z = L/2 \cos \phi$, at which locations a target of diameter L, equal to a length of each transducer is completely illuminated and the Y dimension, perpendicular to the plane of figure, is covered by scanning. This scanning is accomplished since the scanning head containing the two transducers is connected to the mechanical arm which allows both translational and rotational motion. The position and orientation of the transducer are monitored by potentiometers linked to the mechanical arm and displacement means, and these, in turn, control the instantaneous position and orientation of the displayed image.

In order to analyze the process of visualizing a target area, the origin point 0 and an arbitrary point P on the target will be considered. The line OP is imaged by a first transducer 24 as $P_1$ and a second transducer 26 as $P_2$ as is shown in FIG. 2. An analysis of this figure shows that:

$$P_1 = r \cos(\theta + \phi) = g_o \cos\phi - h_o \sin\phi$$
$$P_2 = r \cos(\theta + \phi) = g_o \cos\phi + h_o \sin\phi \quad (1)$$

Thus, a pair of ultrasonic perspectives contains, in optically encoded form information about the coordinates ($g_o$, $h_o$) of P in the plane of the figure, and as previously stated, a third dimension is obtained by scanning.

Figure 3:
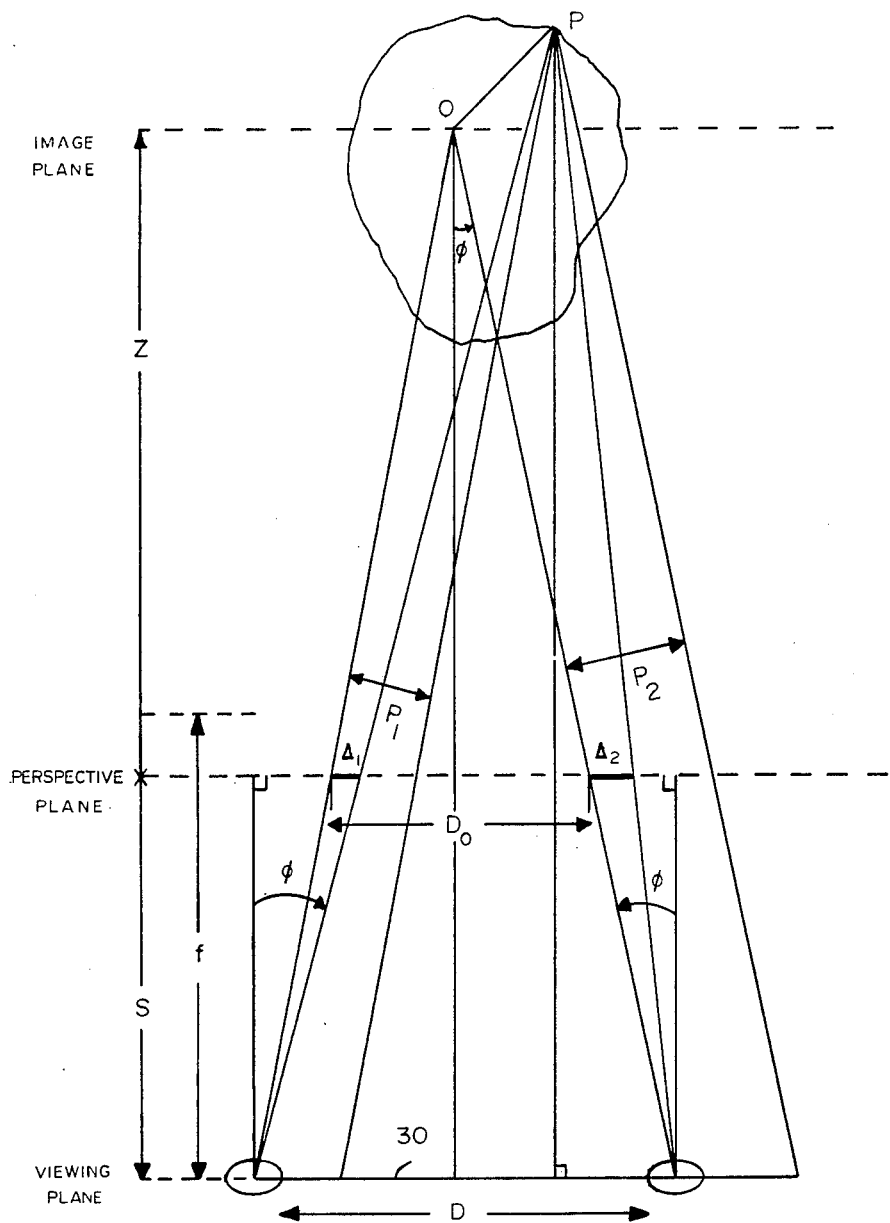

To view a life-size 3D reconstruction of the target 28, the perspective images $P_1$ and $P_2$ are reduced to sizes $\Delta_1$ and $\Delta_2$ and placed in a stereo view 30 as shown in FIG. 3. The observer's eyes are separated by a distance D, and view the perspectives $\Delta_1$ and $\Delta_2$, separated by a distance $D_o$, through positive lenses of focal length $f$. As shown in this figure, the perspective plane is at a distance S from the viewing plane and the origin O of the target is reconstructed at a distance Z + S from the viewing plane.

In order to properly reconstruct O and P, the following requirements must be met:

$$Z + S = D/(2\tan\phi) \quad (2)$$
$$f = \frac{S(Z+S)}{Z}$$
$$D_o = \frac{Z}{Z+S} D$$
$$\frac{\Delta_1}{P_1} = \frac{S}{(Z+S)\cos\phi} = \mu$$
$$\frac{\Delta_2}{P_2} = \frac{S}{(Z+S)\cos\phi} = \mu$$

These equations indicate that the viewer-to-target distance Z + S is determined by the eye separation D and the stereoscopic angle $\phi$. The perspective images are downscaled by the factor $\mu$ and the perspective images of the origin O are symmetrically located around the stereoscopic axis, separated by a distance $D_o$. The focal length of the eye pieces is somewhat larger than the viewer-to-perspective-plane distance and therefore utilizing this arrangement, a three dimensional life-size image of the target is reconstructed. Further, it should be noted that if magnified or reduced images are desired, different geometries can be utilized. Therefore, this mathematical model shows that an area having different properties than the surrounding material can be detected and located in three dimensions.

Figure 4:
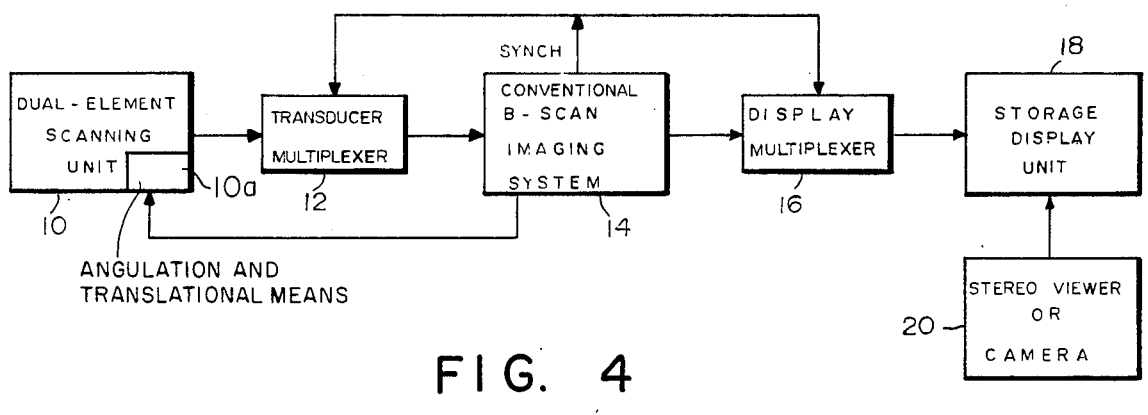
FIG. 4 is a block diagram of the scanning unit.

FIG. 4 shows a block diagram of the different equipment which should be used in recreating a life-size three-dimensional image of the target. A dual element scanning unit 10 is electrically connected to a transducer multiplexer 12 which is connected to, an in synchronization with a conventional B-scan imaging system 14 and a display multiplexer 16. The scanning unit 10 includes the scanning head and an angulation and translational means 10a connected between the head itself and the system 14. The transducer multiplexer 12 has been used in order to avoid the need for a separate receiver channel for each of the transducers, and employs a standard time-division system in which a single receiver alternatively processes each of the transducer outputs. For example, at a 500 Hz pulse rate, the receiver processes the output of one of the transducers for two milliseconds, and the output for the other transducer for the next two milliseconds. This is accomplished by using synchronizing signals, obtained by the B-scanner 14 to trigger a mechanical or solid-state switch capable of handling both the high voltage energizing pulse (typically 500 volts) applied to the transducer and the low level signals (typically 10 $\mu$ volts - 500 millivolts) obtained from the transducer.

The display multiplexer 16 is connected to a standard storage display 18 such as a Tektronix 60 storage monitor which accepts the X, Y and Z axis input signals to generate a display upon a viewing screen in the display unit. The multiplexer 16 receives the X, Y and Z axis signals generated by the conventional B-scanner 14 and produces new X, Y and Z axis signals which gives a split screen display. Synchronized by timing signals obtained from the B-scanner, the display multiplexer 16 applies information acquired from the left transducer to the left side of the screen and information obtained from the right transducer to the right side of the screen. The multiplexer also controls the center-to-center perspective spacing $D_o$, while image scaling $\mu$ as well as the time delay to the center of the first perspective are controlled by the B-scanner 14 itself.

With the help of the multiplexer 16, the split screen display is generated by two electronic steps. The first step is to apply a bias voltage to a horizontal deflection circuit contained in the display unit 18 drawing one of the transducer cycles to shift the image to the right hand side of the display screen. The next step required for the X configuration but not the V configuration is to apply a bias voltage to the vertical deflection circuitry of the display unit 18 during the same transducer cycle to compensate for the stacking of the transducer above the other. Both the horizontal and vertical bias are readily obtained by standard step voltage circuitry synchronized to the multiplex switching circuitry.

A stereo viewer or camera 20 is attached to the display unit 18 so that the observer may correctly view a life size 3-dimensional representation of the target. Many different devices can be used for this purpose, but it has been found that an Austin Photo-Interpretometer gives quite satisfactory results. It is also found that the lens separation can be variable over a range from 60 to 80 mm, and a satisfactory focal length is 120 mm. If a permanent record is desired, a camera, such as Tectronix C-5 oscilloscope camera, can be attached to the display unit face plate 18 and a polaroid photograph recorded.

If a breast analysis is desired, the entire scanning head is mounted on the same type of mechanical arm that is used in conventional ultrasonic tomography and is then immersed in a water tank, one side of which can be replaced by a thin ribbon membrane on Mylar film or other suitable substance. The breast is placed against the membrane which couples the ultrasound to and from the breast. This procedure insures patient comfort since no immersion of the patient is necessary. A perspective scan of the breast is accomplished in a manner similar to the conventional scanning process, except that the two transducers rotate in tandem.

Alternatively, the patient can wear a special formfitting brassiere made of extremely thin, stretchable material. this brassiere can then be mounted on the side of or on top of the water tank.

It will be understood that while certain preferred means have been mentioned with respect to various components of the invention, various changes can be made which will be apparent to those skilled in the art.

It will be obvious to those skilled in the art that various changes may be made without departing from the scope of the invention and the invention is not to be considered limited to what is shown in the drawings and described in the specification.

What is claimed is:

1. An ultrasonic imaging device for undistorted three-dimensional visualization of an object comprising:
   generating means for producing high voltage electrical signals;
   a scanning head containing two, cylindrically focused transducers, each of said cylindrically focused transducers being connected to said generating means, and wherein each of said transducers converts said electrical signals into mechanical energy, transmits said mechanical energy toward the object, receives reflected mechanical energy signals from material of the object, and converts the received mechanical energy into electrical pulses;
   scanning means connected to said transducers for scanning the object and producing respective ultrasonic perspectives thereof from each of said transducers;
   display means connected to said scanning means for displaying each of said ultrasonic perspectives; and
   stereo viewing means attached to said display means for visualizing a three-dimensional, undistorted image formed by said ultrasonic perspectives.

2. A device in accordance with claim 1 further including angulation and translational means connected between said scanning head and scanning means for mechanically moving said scanning head so that the entire area of the object can be scanned.

3. A device in accordance with claim 1 further comprising:
   transducer multiplexer means connected to said generating means and said scanning head for transmitting said high voltage electrical pulses to each of said cylindrically focused transducers in a predetermined sequence; and
   display multiplexer means connected between said transducers and said display means for synchronizing the pulses received from said transducers to ensure proper display on said display means, said display means allowing the pulses received from one of said transducers to be displayed on one portion of said display means, and allowing the pulses received from the other of the transducers to be displayed on a second portion of said display means.

4. A device according to claim 1 further including a recordation means attached to said stereo viewing means for obtaining a permanent record of the data displayed on said display means.

5. A scanning head for undistorted, three-dimensional, ultrasonic imaging of a target comprising:
   a holder; and
   two, cylindrically focused transducers mounted in said holder, each of said transducers having an axis of propagation, an axis of scan and an axis of projection, said transducers being arranged in a configuration in which they make an angle of less than 180° with respect to one another.

6. A scanning head for undistorted, three-dimensional ultrasonic imaging of a target, comprising:
   a holder; and
   two, cylindrically focused transducers mounted in said holder, each of said transducers having an axis of propagation, an axis of scan and an axis of projection, said transducers are being arranged in a "V" configuration.

7. A scanning head for undistorted, three-dimensional ultrasonic imaging of a target, comprising:
   a holder; and
   two, cylindrically focused transducers mounted in said holder, each of said transducers having an axis of propagation, an axis of scan and an axis of projection, said transducers being arranged in an "X" configuration with one of said transducers mounted slightly above the other of said transducers and having its axis of propagation slightly offset with respect to said first transducer.

* * * * *